United States Patent
Boulais et al.

(10) Patent No.: US 8,353,860 B2
(45) Date of Patent: Jan. 15, 2013

(54) DEVICE FOR OBSTRUCTION REMOVAL WITH SPECIFIC TIP STRUCTURE

(75) Inventors: Dennis R Boulais, Danielson, CT (US); Michael S Banik, Bolton, MA (US); Vincent Turturro, Bolton, MA (US); Christopher Rowland, Hopkinton, MA (US); David W Hoffman, Concord, MA (US); John P O'Connor, Andover, MA (US); Lucien A Couvillon, Jr., Concord, MA (US); Mark L Adams, Sandy, UT (US); William J Shaw, Cambridge, MA (US); Donald C Hovey, Sherborn, MA (US); Luis J Maseda, Natick, MA (US); Laurence D Brenner, Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 269 days.

(21) Appl. No.: 11/241,829

(22) Filed: Sep. 30, 2005

(65) Prior Publication Data
US 2006/0173244 A1    Aug. 3, 2006

Related U.S. Application Data

(60) Provisional application No. 60/614,929, filed on Sep. 30, 2004.

(51) Int. Cl.
*A61M 3/00* (2006.01)
*A61M 1/00* (2006.01)
(52) U.S. Cl. .......................................... 604/43; 604/27
(58) Field of Classification Search ..................... 604/22, 604/27, 39, 43
See application file for complete search history.

(56) References Cited

U.S. PATENT DOCUMENTS

| | | | |
|---|---|---|---|
| 2,791,218 A * | 5/1957 | Nimmo | 604/39 |
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,425,113 A | 1/1984 | Bilstad | |
| 4,428,748 A * | 1/1984 | Peyman et al. | 604/22 |

(Continued)

FOREIGN PATENT DOCUMENTS
EP     0 689 851 A1     1/1996
(Continued)

*Primary Examiner* — Kevin C Sirmons
*Assistant Examiner* — Bradley Osinski
(74) *Attorney, Agent, or Firm* — Bookoff McAndrews, PLLC

(57) ABSTRACT

In one aspect, the present invention is a system for preparing a patient for an endoscopy procedure, such as a colonoscopy. The endoscopic preparation and examination system includes an endoscope, a source of irrigation and aspiration, and a control unit. The endoscope includes an elongated flexible shaft with a distal tip and a proximal end, at least one aspiration lumen and at least one irrigation lumen. A plurality of irrigation ports are functionally connected to the at least one irrigation lumen and a plurality of aspiration ports are functionally connected to the at least one aspiration lumen. In another aspect, the invention provides a method of clearing an obstructed view in a patient prior to, or during an endoscopic examination.

17 Claims, 9 Drawing Sheets

U.S. PATENT DOCUMENTS

| | | | |
|---|---|---|---|
| 4,432,349 A | 2/1984 | Oshiro | |
| 4,447,227 A | 5/1984 | Kotsanis | |
| 4,471,766 A | 9/1984 | Terayama | |
| 4,473,841 A | 9/1984 | Murakoshi et al. | |
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,621,618 A | 11/1986 | Omagari et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,652,916 A | 3/1987 | Suzaki et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,728,319 A * | 3/1988 | Masch | 604/22 |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okobe | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,836,187 A | 6/1989 | Iwakoshi et al. | |
| 4,842,583 A | 6/1989 | Majlessi | |
| 4,844,052 A | 7/1989 | Iwakoshi et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,893,634 A | 1/1990 | Kulik et al. | |
| 4,894,715 A | 1/1990 | Uchikubo et al. | |
| 4,895,431 A | 1/1990 | Tsujiuchi et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A | 11/1990 | Doi et al. | |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,022,382 A | 6/1991 | Ohshoki et al. | |
| 5,029,016 A | 7/1991 | Hiyama et al. | |
| 5,034,888 A | 7/1991 | Uehara et al. | |
| 5,040,069 A | 8/1991 | Matsumoto et al. | |
| RE33,689 E | 9/1991 | Nishioka et al. | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki | |
| 5,061,994 A | 10/1991 | Takahashi | |
| 5,068,719 A | 11/1991 | Tsuji | |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,170,775 A | 12/1992 | Tagami | |
| 5,172,225 A | 12/1992 | Takahashi et al. | |
| 5,174,293 A | 12/1992 | Hagiwara | |
| 5,176,629 A | 1/1993 | Kullas et al. | |
| 5,178,606 A | 1/1993 | Ognier et al. | |
| 5,191,878 A | 3/1993 | Iida et al. | |
| 5,198,931 A | 3/1993 | Igarashi | |
| 5,201,908 A | 4/1993 | Jones | |
| 5,208,702 A | 5/1993 | Shiraiwa | |
| 5,209,220 A | 5/1993 | Hiyama et al. | |
| 5,225,958 A | 7/1993 | Nakamura | |
| 5,228,356 A | 7/1993 | Chuang | |
| 5,243,416 A | 9/1993 | Nakazawa | |

| | | | | | | |
|---|---|---|---|---|---|---|
| 5,243,967 | A | 9/1993 | Hibino | 5,781,172 A | 7/1998 | Engel et al. |
| 5,257,628 | A | 11/1993 | Ishiguro et al. | 5,788,714 A | 8/1998 | Ouchi |
| 5,271,381 | A | 12/1993 | Ailinger et al. | 5,789,047 A | 8/1998 | Sasaki et al. |
| RE34,504 | E | 1/1994 | Uehara et al. | 5,793,539 A | 8/1998 | Konno et al. |
| 5,279,542 | A | 1/1994 | Wilk | 5,805,140 A | 9/1998 | Rosenberg et al. |
| 5,284,486 | A * | 2/1994 | Kotula et al. .............. 606/159 | 5,807,240 A | 9/1998 | Muller et al. |
| 5,290,279 | A | 3/1994 | Bonati | 5,810,715 A | 9/1998 | Moriyama |
| 5,291,010 | A | 3/1994 | Tsuji | 5,812,983 A | 9/1998 | Kumagai |
| 5,299,559 | A | 4/1994 | Bruce et al. | 5,819,736 A | 10/1998 | Avny et al. |
| 5,311,858 | A | 5/1994 | Adair | 5,820,591 A | 10/1998 | Thompson et al. |
| 5,325,845 | A | 7/1994 | Adair et al. | 5,821,466 A | 10/1998 | Clark et al. |
| 5,331,551 | A | 7/1994 | Tsuruoka et al. | 5,821,920 A | 10/1998 | Rosenberg et al. |
| 5,342,299 | A | 8/1994 | Snoke et al. | 5,823,940 A | 10/1998 | Newman |
| 5,347,989 | A | 9/1994 | Monroe et al. | 5,823,948 A | 10/1998 | Ross, Jr. et al. |
| 5,354,302 | A | 10/1994 | Ko | 5,827,186 A | 10/1998 | Chen et al. |
| 5,374,953 | A | 12/1994 | Sasaki et al. | 5,827,190 A | 10/1998 | Palcic et al. |
| 5,379,757 | A | 1/1995 | Hiyama et al. | 5,827,203 A * | 10/1998 | Nita .............................. 601/2 |
| 5,381,782 | A | 1/1995 | DeLaRama et al. | 5,828,197 A | 10/1998 | Martin et al. |
| 5,390,662 | A | 2/1995 | Okada | 5,828,363 A | 10/1998 | Yaniger et al. |
| 5,395,316 | A * | 3/1995 | Martin ........................ 604/43 | 5,830,124 A | 11/1998 | Suzuki et al. |
| 5,400,769 | A | 3/1995 | Tanii et al. | 5,830,128 A | 11/1998 | Tanaka |
| 5,402,768 | A | 4/1995 | Adair | 5,836,869 A | 11/1998 | Kudo et al. |
| 5,402,769 | A | 4/1995 | Tsuji | 5,837,023 A | 11/1998 | Koike et al. |
| 5,405,319 | A | 4/1995 | Abell et al. | 5,840,014 A | 11/1998 | Miyano et al. |
| 5,409,485 | A | 4/1995 | Suda | 5,841,126 A | 11/1998 | Fossum et al. |
| 5,412,478 | A | 5/1995 | Ishihara et al. | 5,843,000 A | 12/1998 | Nishioka et al. |
| 5,418,649 | A | 5/1995 | Igarashi | 5,846,183 A | 12/1998 | Chilcoat |
| 5,420,644 | A | 5/1995 | Watanabe | 5,855,560 A | 1/1999 | Idaomi et al. |
| 5,431,645 | A | 7/1995 | Smith et al. | 5,857,963 A | 1/1999 | Pelchy et al. |
| 5,434,615 | A | 7/1995 | Matsumoto | 5,865,724 A | 2/1999 | Palmer et al. |
| 5,436,640 | A | 7/1995 | Reeves | 5,868,664 A | 2/1999 | Speier et al. |
| 5,436,767 | A | 7/1995 | Suzuki et al. | 5,868,666 A | 2/1999 | Okada et al. |
| 5,440,341 | A | 8/1995 | Suzuki et al. | 5,873,816 A | 2/1999 | Kagawa et al. |
| 5,464,007 | A | 11/1995 | Krauter et al. | 5,873,866 A | 2/1999 | Kondo et al. |
| 5,469,840 | A | 11/1995 | Tanii et al. | 5,876,326 A | 3/1999 | Takamura et al. |
| 5,473,235 | A | 12/1995 | Lance et al. | 5,876,331 A | 3/1999 | Wu et al. |
| 5,482,029 | A | 1/1996 | Sekiguchi et al. | 5,876,373 A | 3/1999 | Giba et al. |
| 5,484,407 | A | 1/1996 | Osypka | 5,876,427 A | 3/1999 | Chen et al. |
| 5,485,316 | A | 1/1996 | Mori et al. | 5,877,819 A | 3/1999 | Branson |
| 5,496,260 | A | 3/1996 | Krauter et al. | 5,879,284 A | 3/1999 | Tsujita |
| 5,515,449 | A | 5/1996 | Tsuruoka et al. | 5,880,714 A | 3/1999 | Rosenberg et al. |
| 5,518,501 | A | 5/1996 | Oneda et al. | 5,882,293 A | 3/1999 | Ouchi |
| 5,543,831 | A | 8/1996 | Tsuji et al. | 5,882,339 A | 3/1999 | Beiser et al. |
| 5,569,158 | A | 10/1996 | Suzuki et al. | 5,889,670 A | 3/1999 | Schuler et al. |
| 5,569,159 | A | 10/1996 | Anderson et al. | 5,889,672 A | 3/1999 | Schuler et al. |
| 5,586,262 | A | 12/1996 | Komatsu et al. | 5,892,630 A | 4/1999 | Broome |
| 5,589,854 | A | 12/1996 | Tsai | 5,895,350 A | 4/1999 | Hori |
| 5,591,202 | A | 1/1997 | Slater et al. | 5,897,507 A | 4/1999 | Kortenbach et al. |
| 5,608,451 | A | 3/1997 | Konno et al. | 5,897,525 A | 4/1999 | Dey et al. |
| 5,619,380 | A | 4/1997 | Agasawa et al. | 5,907,487 A | 5/1999 | Rosenberg et al. |
| 5,622,528 | A | 4/1997 | Hamano et al. | 5,923,018 A | 7/1999 | Kameda et al. |
| 5,631,695 | A | 5/1997 | Nakamura et al. | 5,928,136 A | 7/1999 | Barry |
| 5,633,203 | A | 5/1997 | Adair | 5,929,607 A | 7/1999 | Rosenberg et al. |
| 5,643,203 | A | 7/1997 | Beiser et al. | 5,929,846 A | 7/1999 | Rosenberg et al. |
| 5,645,075 | A | 7/1997 | Palmer et al. | 5,929,900 A | 7/1999 | Yamanaka |
| 5,647,840 | A | 7/1997 | D'Amelio et al. | 5,929,901 A | 7/1999 | Adair et al. |
| 5,658,238 | A | 8/1997 | Suzuki et al. | 5,931,833 A | 8/1999 | Silverstein |
| 5,667,477 | A | 9/1997 | Segawa | 5,933,809 A | 8/1999 | Hunt et al. |
| 5,674,182 | A | 10/1997 | Suzuki et al. | 5,935,085 A | 8/1999 | Welsh et al. |
| 5,674,197 | A | 10/1997 | van Muiden et al. | 5,936,778 A | 8/1999 | Miyano et al. |
| 5,685,823 | A | 11/1997 | Ito et al. | 5,941,817 A | 8/1999 | Crawford |
| 5,685,825 | A | 11/1997 | Takase et al. | 5,950,168 A | 9/1999 | Simborg et al. |
| 5,691,853 | A | 11/1997 | Miyano | 5,951,462 A | 9/1999 | Yamanaka |
| 5,695,450 | A | 12/1997 | Yabe et al. | 5,956,416 A | 9/1999 | Tsuruoka et al. |
| 5,698,866 | A | 12/1997 | Doiron et al. | 5,956,689 A | 9/1999 | Everhart |
| 5,702,349 | A | 12/1997 | Morizumi | 5,956,690 A | 9/1999 | Haggerson et al. |
| 5,703,724 | A | 12/1997 | Miyano | 5,959,613 A | 9/1999 | Rosenberg et al. |
| 5,704,371 | A | 1/1998 | Shepard | 5,976,070 A | 11/1999 | Ono et al. |
| 5,704,896 | A | 1/1998 | Fukunishi et al. | 5,976,074 A | 11/1999 | Moriyama |
| 5,708,482 | A | 1/1998 | Takahashi et al. | 5,980,454 A | 11/1999 | Broome |
| 5,721,566 | A | 2/1998 | Rosenberg et al. | 5,980,468 A | 11/1999 | Zimmon |
| 5,724,068 | A | 3/1998 | Sanchez et al. | 5,986,693 A | 11/1999 | Adair et al. |
| 5,728,045 | A | 3/1998 | Komi | 5,991,729 A | 11/1999 | Barry et al. |
| 5,739,811 | A | 4/1998 | Rosenberg et al. | 5,991,730 A | 11/1999 | Lubin et al. |
| 5,740,801 | A | 4/1998 | Branson | 5,999,168 A | 12/1999 | Rosenberg et al. |
| 5,746,696 | A | 5/1998 | Kondo | 6,002,425 A | 12/1999 | Yamanaka et al. |
| 5,764,809 | A | 6/1998 | Nomami et al. | 6,007,531 A | 12/1999 | Snoke et al. |
| 5,767,839 | A | 6/1998 | Rosenberg | 6,014,630 A | 1/2000 | Jeacock et al. |
| 5,769,816 | A | 6/1998 | Barbut et al. | 6,015,088 A | 1/2000 | Parker et al. |

| | | | | | | |
|---|---|---|---|---|---|---|
| 6,017,322 | A | 1/2000 | Snoke et al. | 6,454,162 B1 | 9/2002 | Teller |
| 6,020,875 | A | 2/2000 | Moore et al. | 6,459,447 B1 | 10/2002 | Okada et al. |
| 6,020,876 | A | 2/2000 | Rosenberg et al. | 6,468,204 B2 | 10/2002 | Sendai et al. |
| 6,026,363 | A | 2/2000 | Shepard | 6,475,141 B2 | 11/2002 | Abe |
| 6,030,360 | A | 2/2000 | Biggs | 6,478,730 B1 | 11/2002 | Bala et al. |
| 6,032,120 | A | 2/2000 | Rock et al. | 6,489,987 B1 | 12/2002 | Higuchi et al. |
| 6,039,728 | A | 3/2000 | Berlien et al. | 6,496,827 B2 | 12/2002 | Kozam et al. |
| 6,043,839 | A | 3/2000 | Adair et al. | 6,498,948 B1 | 12/2002 | Ozawa et al. |
| 6,050,718 | A | 4/2000 | Schena et al. | 6,503,193 B1 | 1/2003 | Iwasaki et al. |
| 6,057,828 | A | 5/2000 | Rosenberg et al. | 6,520,908 B1 | 2/2003 | Ikeda et al. |
| 6,059,719 | A | 5/2000 | Yamamoto et al. | 6,524,234 B2 | 2/2003 | Ouchi |
| 6,061,004 | A | 5/2000 | Rosenberg | 6,530,882 B1 | 3/2003 | Farkas et al. |
| 6,067,077 | A | 5/2000 | Martin et al. | 6,533,722 B2 | 3/2003 | Nakashima |
| 6,071,248 | A | 6/2000 | Zimmon | 6,540,669 B2 | 4/2003 | Abe et al. |
| 6,075,555 | A | 6/2000 | Street | 6,544,194 B1 | 4/2003 | Kortenbach et al. |
| 6,078,308 | A | 6/2000 | Rosenberg et al. | 6,545,703 B1 | 4/2003 | Takahashi et al. |
| 6,078,353 | A | 6/2000 | Yamanaka et al. | 6,551,239 B2 | 4/2003 | Renner et al. |
| 6,078,876 | A | 6/2000 | Rosenberg et al. | 6,558,317 B2 | 5/2003 | Takahashi et al. |
| 6,080,104 | A | 6/2000 | Ozawa et al. | 6,561,971 B1 | 5/2003 | Akiba |
| 6,081,809 | A | 6/2000 | Kumagai | 6,565,507 B2 | 5/2003 | Kamata et al. |
| 6,083,152 | A | 7/2000 | Strong | 6,574,629 B1 | 6/2003 | Cooke, Jr. et al. |
| 6,083,170 | A | 7/2000 | Ben-Haim | 6,589,162 B2 | 7/2003 | Nakashima et al. |
| 6,095,971 | A | 8/2000 | Takahashi | 6,595,913 B2 | 7/2003 | Takahashi |
| 6,099,465 | A | 8/2000 | Inoue | 6,597,390 B1 | 7/2003 | Higuchi |
| 6,100,874 | A | 8/2000 | Schena et al. | 6,599,239 B2 | 7/2003 | Hayakawa et al. |
| 6,104,382 | A | 8/2000 | Martin et al. | 6,602,186 B1 | 8/2003 | Sugimoto et al. |
| 6,120,435 | A | 9/2000 | Eino | 6,605,035 B2 | 8/2003 | Ando et al. |
| 6,125,337 | A | 9/2000 | Rosenberg et al. | 6,609,135 B1 | 8/2003 | Omori et al. |
| 6,128,006 | A | 10/2000 | Rosenberg et al. | 6,611,846 B1 | 8/2003 | Stoodley |
| 6,129,701 | A | 10/2000 | Cimino | 6,614,969 B2 | 9/2003 | Eichelberger et al. |
| 6,132,369 | A | 10/2000 | Takahashi | 6,616,601 B2 | 9/2003 | Hayakawa |
| 6,134,056 | A | 10/2000 | Nakamura | 6,623,424 B2 | 9/2003 | Hayakawa et al. |
| 6,134,506 | A | 10/2000 | Rosenberg et al. | 6,635,034 B1 | 10/2003 | Cosmescu |
| 6,135,946 | A | 10/2000 | Konen et al. | 6,638,214 B2 | 10/2003 | Akiba |
| 6,139,508 | A | 10/2000 | Simpson et al. | 6,638,215 B2 | 10/2003 | Kobayashi |
| 6,141,037 | A | 10/2000 | Upton et al. | 6,641,528 B2 | 11/2003 | Torii |
| 6,142,956 | A | 11/2000 | Kortenbach et al. | 6,651,669 B1 | 11/2003 | Burnside |
| 6,146,355 | A | 11/2000 | Biggs | 6,656,110 B1 | 12/2003 | Irion et al. |
| 6,149,607 | A | 11/2000 | Simpson et al. | 6,656,112 B2 | 12/2003 | Miyanaga |
| 6,152,877 | A | 11/2000 | Masters | 6,659,940 B2 | 12/2003 | Adler |
| 6,154,198 | A | 11/2000 | Rosenberg | 6,663,561 B2 | 12/2003 | Sugimoto et al. |
| 6,154,248 | A | 11/2000 | Ozawa et al. | 6,669,629 B2 | 12/2003 | Matsui |
| 6,155,988 | A | 12/2000 | Peters | 6,673,012 B2 | 1/2004 | Fujii et al. |
| 6,181,481 | B1 | 1/2001 | Yamamoto et al. | 6,677,984 B2 | 1/2004 | Kobayashi et al. |
| 6,184,922 | B1 | 2/2001 | Saito et al. | 6,678,397 B1 | 1/2004 | Omori et al. |
| 6,193,714 | B1 | 2/2001 | McGaffigan et al. | 6,682,479 B1 | 1/2004 | Takahashi et al. |
| 6,195,592 | B1 | 2/2001 | Schuler et al. | 6,685,631 B2 | 2/2004 | Minami |
| 6,203,493 | B1 | 3/2001 | Ben-Haim | 6,686,949 B2 | 2/2004 | Kobayashi et al. |
| 6,206,824 | B1 | 3/2001 | Ohara et al. | 6,690,409 B1 | 2/2004 | Takahashi |
| 6,211,904 | B1 | 4/2001 | Adair | 6,690,963 B2 | 2/2004 | Ben-Haim et al. |
| 6,216,104 | B1 | 4/2001 | Moshfeghi et al. | 6,692,431 B2 | 2/2004 | Kazakevich |
| 6,219,091 | B1 | 4/2001 | Yamanaka et al. | 6,697,101 B1 | 2/2004 | Takahashi et al. |
| 6,221,070 | B1 | 4/2001 | Tu et al. | 6,699,181 B2 | 3/2004 | Wako |
| 6,241,668 | B1 | 6/2001 | Herzog | 6,702,737 B2 | 3/2004 | Hino et al. |
| 6,260,994 | B1 | 7/2001 | Matsumoto et al. | 6,711,426 B2 | 3/2004 | Benaron et al. |
| 6,272,470 | B1 | 8/2001 | Teshima | 6,715,068 B1 | 3/2004 | Abe |
| 6,275,255 | B1 | 8/2001 | Adair et al. | 6,716,162 B2 | 4/2004 | Hakamata |
| 6,283,960 | B1 | 9/2001 | Ashley | 6,719,717 B1 | 4/2004 | Johnson |
| 6,295,082 | B1 | 9/2001 | Dowdy et al. | 6,728,599 B2 | 4/2004 | Wang et al. |
| 6,299,625 | B1 | 10/2001 | Bacher | 6,730,018 B2 | 5/2004 | Takase |
| 6,309,347 | B1 | 10/2001 | Takahashi et al. | 6,736,773 B2 | 5/2004 | Wendlandt et al. |
| 6,309,399 | B1 | 10/2001 | Barbut et al. | 6,743,240 B2 | 6/2004 | Smith et al. |
| 6,310,642 | B1 | 10/2001 | Adair et al. | 6,749,559 B1 | 6/2004 | Krass et al. |
| 6,319,196 | B1 | 11/2001 | Minami | 6,749,560 B1 | 6/2004 | Konstorum et al. |
| 6,319,197 | B1 | 11/2001 | Tsuji et al. | 6,749,561 B2 | 6/2004 | Kazakevich |
| 6,334,844 | B1 | 1/2002 | Akiba | 6,753,905 B1 | 6/2004 | Okada et al. |
| 6,346,075 | B1 | 2/2002 | Arai et al. | 6,758,806 B2 | 7/2004 | Kamrava et al. |
| 6,366,799 | B1 | 4/2002 | Acker et al. | 6,758,807 B2 | 7/2004 | Minami |
| 6,381,029 | B1 | 4/2002 | Tipirneni | 6,758,842 B2 | 7/2004 | Irion et al. |
| 6,398,724 | B1 | 6/2002 | May et al. | 6,778,208 B2 | 8/2004 | Takeshige et al. |
| 6,413,207 | B1 | 7/2002 | Minami | 6,780,151 B2 | 8/2004 | Grabover et al. |
| 6,421,078 | B1 | 7/2002 | Akai et al. | 6,785,410 B2 | 8/2004 | Vining et al. |
| 6,425,535 | B1 | 7/2002 | Akiba | 6,785,593 B2 | 8/2004 | Wang et al. |
| 6,425,858 | B1 | 7/2002 | Minami | 6,796,938 B2 | 9/2004 | Sendai |
| 6,436,032 | B1 | 8/2002 | Eto et al. | 6,796,939 B1 | 9/2004 | Hirata et al. |
| 6,441,845 | B1 | 8/2002 | Matsumoto | 6,798,533 B2 | 9/2004 | Tipirneni |
| 6,447,444 | B1 | 9/2002 | Avni et al. | 6,800,056 B2 | 10/2004 | Tartaglia et al. |
| 6,449,006 | B1 | 9/2002 | Shipp | 6,800,057 B2 | 10/2004 | Tsujita et al. |
| 6,453,190 | B1 | 9/2002 | Acker et al. | 6,808,491 B2 | 10/2004 | Kortenbach et al. |

| | | |
|---|---|---|
| 6,824,539 B2 | 11/2004 | Novak |
| 6,824,548 B2 | 11/2004 | Smith et al. |
| 6,829,003 B2 | 12/2004 | Takami |
| 6,830,545 B2 | 12/2004 | Bendall |
| 6,832,990 B2 | 12/2004 | Kortenbach et al. |
| 6,840,932 B2 | 1/2005 | Lang et al. |
| 6,842,196 B1 | 1/2005 | Swift et al. |
| 6,846,286 B2 | 1/2005 | Suzuki et al. |
| 6,847,933 B1 | 1/2005 | Hastings |
| 6,849,043 B2 | 2/2005 | Kondo |
| 6,850,794 B2 | 2/2005 | Shahidi |
| 6,855,109 B2 | 2/2005 | Obata et al. |
| 6,858,004 B1 | 2/2005 | Ozawa et al. |
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B2 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0058904 A1 * | 5/2002 | Boock et al. .................... 604/35 |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0123761 A1 | 9/2002 | Barbut |
| 2002/0128633 A1 | 9/2002 | Brock et al. |
| 2002/0151906 A1 * | 10/2002 | Demarais et al. ............. 606/128 |
| 2002/0193664 A1 | 12/2002 | Ross et al. |
| 2003/0032863 A1 | 2/2003 | Kazakevich |
| 2003/0069897 A1 | 4/2003 | Roy et al. |
| 2003/0130613 A1 | 7/2003 | Harmon et al. |
| 2003/0149338 A1 | 8/2003 | Francois et al. |
| 2003/0181905 A1 | 9/2003 | Long |
| 2003/0199736 A1 | 10/2003 | Christopher |
| 2004/0039348 A1 | 2/2004 | Kim et al. |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Meada et al. |
| 2004/0073085 A1 | 4/2004 | Ikeda et al. |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0197861 A1 | 9/2005 | Omori et al. |
| 2005/0203341 A1 | 9/2005 | Welker et al. |
| 2005/0228697 A1 | 10/2005 | Funahashi |
| 2005/0256464 A1 | 11/2005 | Pallas |

FOREIGN PATENT DOCUMENTS

| | | | |
|---|---|---|---|
| EP | 1 300 883 | A2 | 4/2003 |
| JP | 58-78635 | A | 5/1983 |
| JP | 05-31071 | A | 2/1993 |
| JP | 05-091972 | A | 4/1993 |
| JP | 06-105800 | | 4/1994 |
| JP | 06-254048 | A | 9/1994 |
| JP | 07-8441 | A | 1/1995 |
| JP | 10-113330 | A | 5/1998 |
| JP | 10-286221 | A | 10/1998 |
| JP | 11-216113 | A | 8/1999 |
| JP | 3219521 | B2 | 8/2001 |
| JP | 2002-102152 | A | 4/2002 |
| JP | 2002-177197 | A | 6/2002 |
| JP | 2002-185873 | A | 6/2002 |
| JP | 2002-253481 | A | 9/2002 |
| JP | 3372273 | B2 | 11/2002 |
| JP | 2003-75113 | A | 3/2003 |
| JP | 3482238 | B2 | 10/2003 |
| WO | WO 93/13704 | A1 | 7/1993 |
| WO | 9505112 | A1 | 2/1995 |
| WO | WO 2004/016310 | A2 | 2/2004 |
| WO | WO 2005/023082 | A2 | 3/2005 |

* cited by examiner

DEVICE FOR OBSTRUCTION REMOVAL WITH SPECIFIC TIP STRUCTURE

CROSS-REFERENCE TO RELATED APPLICATION

The present application claims the benefit of U.S. Provisional Application No. 60/614,929, filed Sep. 30, 2004.

FIELD OF THE INVENTION

The present invention relates to medical devices in general and to medical devices for obstruction removal and patient examination in particular.

BACKGROUND OF THE INVENTION

It has become well established that there are major public health benefits from regular endoscopic examinations of patients' internal structures such as the alimentary and excretory canals. In any endoscopic procedure, there is always a need for the introduction and evacuation of different types of fluids, such as water, saline, drugs, contrast material, dyes, or emulsifiers. One such endoscopic procedure is a colonoscopy, which is an internal examination of the colon by means of an instrument called a colonoscope. A standard colonoscope is typically 135-185 cm in length and 12-13 mm in diameter and includes a fiber optic imaging bundle, illumination fibers, and an instrument or working channel that may be used for the delivery of tools into the patient and the vacuum evacuation of liquids. The colonoscope is inserted into the colon via the patient's anus and is advanced through the colon, allowing direct visual examination of the colon wall, the ileocecal valve, and portions of the terminal ileum. Approximately six million colonoscopies are performed each year.

In colonoscopic procedures, clear visualization of the entire colon, cecum and rectum is required for the procedure to be effective and efficient. It is estimated that about 20% of all colon polyps in patients are undetected due to low visibility, which can arise from poor colon preparation. Presently, about 10% of all colonoscopy patients are non-compliant with prescribed preparatory procedures and approximately 4% of all patients are unable to complete the exam due to an excess of stool in the colon. The remaining 6% are considered marginal, and the colonoscopy may still be performed if the colon is further evacuated as a part of the procedure. Conventionally, the marginal colons are cleared by repeatedly administering several small (e.g. 60 cc) fluid flushes through an endoscope's working channel by means of an ancillary apparatus that employs a low-volume wash and suction. The waste slurry is then removed with suction through the working channel in the endoscope. This tedious and inefficient process is limited by the amount of stool that can be removed with each flush. The process also causes a loss of productivity due to the added time required to fully evacuate the colon.

Conventional endoscopes are expensive hand-assembled medical devices costing in the range of approximately $25,000 for an endoscope, and much more for the associated operator console. Because of the expense, these endoscopes are built to withstand repeated disinfections and use upon many patients. Conventional endoscopes are generally built of strong composite materials, which decrease the flexibility of the endoscope and thus can compromise patient comfort. Furthermore, conventional endoscopes are complex and fragile instruments that frequently need expensive repair as a result of damage during use or during a disinfection procedure. A problem encountered with conventional endoscopes is the difficulty of sterilization between procedures. Sterilization of endoscopes may be accomplished with an autoclave, however, this tends to be harmful to the polymer components of the probe. Chemical bath sterilization may be used, however, this method cannot ensure complete removal of biological material that may become trapped within the channels of the endoscope probe.

Low cost, disposable medical devices designated for a single use have become popular for instruments that are difficult to sterilize or clean properly. Single use, disposable devices are packaged in sterile wrappers to avoid the risk of pathogenic cross-contamination of diseases such as HIV, hepatitis and other pathogens. Hospitals generally welcome the convenience of single use disposable products because they no longer have to be concerned with product age, overuse, breakage, malfunction and sterilization. One medical device that has not previously been inexpensive enough to be considered truly disposable is the endoscope, such as a colonoscope, ureteroscope, gastroscope, bronchoscope, duodenoscope, etc. Such a single-use or disposable endoscope is described in U.S. patent application Ser. No. 10/406,149 filed Apr. 1, 2003, Ser. No. 10/811,781, filed Mar. 29, 2004, and Ser. No. 10/956,007, filed Sep. 30, 2004, all assigned to Scimed Life Systems, Inc./Boston Scientific Scimed, Inc., which are incorporated herein by reference.

To overcome these and other problems, there is a need for a way to perform an irrigation and evacuation process prior to and/or during an endoscopy procedure upon poorly prepared or non-prepared patients, by use of an endoscope that is capable of preparing the patient and optionally also examining the patient. The endoscope can be reusable, or designed as a low cost endoscope that can be used for a single procedure and thrown away. The preparation and examination endoscope should be simple and easy to use in order to efficiently prepare patients for a colonoscopy procedure.

SUMMARY OF THE INVENTION

To address these and other problems, the present invention is an endoscopic preparation system that includes an endoscope, a source of irrigation and aspiration, and a control unit. In one embodiment, the preparation system comprises an endoscope that is capable of both patient preparation and examination. The endoscope includes an elongated flexible shaft with a distal tip and a proximal end, at least one aspiration lumen and at least one irrigation lumen. A plurality of irrigation ports are functionally connected to the irrigation lumen. The endoscope is removably connected to the source of irrigation and aspiration that are selectively controlled by the control unit to deliver an irrigant through the irrigation lumen and to aspirate the irrigant and other material through the aspiration lumen. In another embodiment, the system comprises a first preparation-specific endoscope and a second imaging endoscope that are each removably connected to a control unit.

In one embodiment, an excising device is disposed in the distal tip of the endoscope. The excising device is capable of mechanically cutting and/or disrupting an obstruction for aspiration in a patient.

In another embodiment, the endoscope includes a trapping device disposed in the distal tip. The trapping device is capable of trapping liquefied or disrupted material to be removed and/or aspirated from a subject.

In another aspect, the present invention is a method of removing an obstruction from a patient prior to, or during an examination. The method involves detecting an obstruction with an imaging endoscope, executing a wash routine comprising irrigation and aspiration of the material forming the obstruction, detecting the removal of the obstruction, optionally examining the patient, removing the endoscope from the patient and optionally disposing of the imaging endoscope. The method is executed with an imaging endoscope comprising at least one irrigation lumen and at least one aspiration lumen.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As indicated above, the present invention is an endoscopic preparation system that provides integrated irrigation and aspiration functions for preparing and optionally examining poorly prepared patients. Although the present invention is described with respect to its use within the colon, it will be appreciated that the invention can be used in any body cavity that may require preparation for examination or surgery. While the invention is described in terms of a preparatory and examination system and apparatus, it will be understood by one of skill in the art that in some embodiments, the endoscope having the features described for obstruction removal is a multifunctional device that may also be used for a variety of different diagnostic and interventional procedures, including colonoscopy, upper endoscopy, bronchoscopy, thoracoscopy, laparoscopy, and video endoscopy, etc. In one embodiment, the endoscope is designed as a preparation-specific endoscope designed for preparing a patient for a procedure such as a colonoscopy.

The various embodiments of the endoscope described herein may be used with both reusable and low cost, disposable endoscopes, such as an endoscope that is sufficiently inexpensive to manufacture such that it can be a single-use device as described in U.S. patent application Ser. No. 10/406,149 filed Apr. 1, 2003, U.S. patent application Ser. No. 10/811,781, filed Mar. 29, 2004, and Ser. No. 10/956,007, filed Sep. 30, 2004, that are assigned to Scimed Life Systems, Inc., now Boston Scientific Scimed, Inc, and are hereby incorporated by reference.

Figure 1:
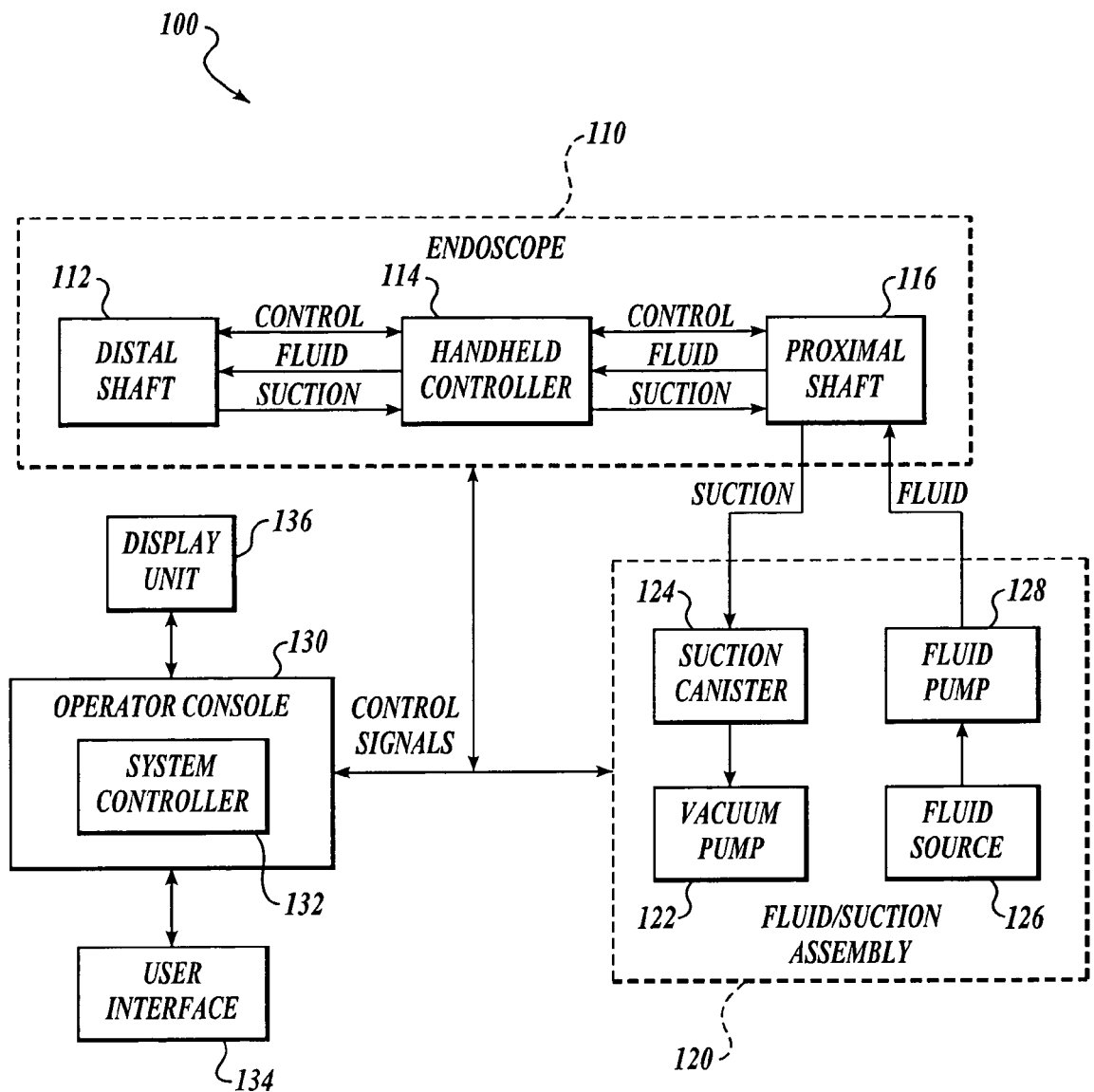
FIG. 1 is a block diagram of an endoscopic preparation and examination system comprising an endoscope with a handheld controller, a fluid/suction assembly and an operator console in accordance with an embodiment of the invention.

FIG. 1 illustrates the major components of an exemplary endoscopic preparation and optional examination system 100. The endoscopic preparation and examination system 100 includes an endoscope 110 that is electrically and fluidly connected to a fluid/suction assembly 120 and to an operator console 130. The endoscope 110 includes a distal shaft 112 with an articulating distal tip, a handheld controller 114, and a proximal shaft 116. The fluid/suction assembly 120 includes a vacuum pump 122, and an in-line suction canister 124 to aspirate liquid/debris from a patient. A fluid source 126 and a fluid pump 128 deliver fluids to the patient. The fluid/suction assembly 120 is electrically connected to the operator console 130. The operator console 130 includes a system controller 132 and is connected to a user interface 134 and a display unit 136.

The fluid/suction assembly 120 is generally described as a special-purpose electro-mechanical apparatus that provides a source of irrigation and aspiration for the endoscopic preparation and examination system 100. As indicated above, the fluid/suction assembly 120 includes a vacuum pump 122 for aspiration, which provides vacuum pressure for a collection device, such as, for example, the suction canister 124. The suction canister 124 may be any suitable waste container capable of holding aspirated material (e.g., fecal matter, bodily fluids, extracted tissue and the like). For example, one such suitable container is a standard container for medical waste that can hold approximately one to four liters (1-4 L) of aspirated material. The fluid/suction assembly 120 further includes a fluid source 126, such as a fluid reservoir or other fluid supply apparatus. The suction canister 124 is typically sized to hold at least two or more times the volume of the fluid source 126. In one exemplary embodiment, the fluid source 126 is capable of holding at least from about one to two liters (1-2 L) of irrigation fluids, such as saline solution, lubricating solution and the like. The fluid pump 128 included in the fluid/suction assembly 120 is capable of delivering a flow rate suitable for irrigation of a body lumen, such as a colon. The fluid/suction assembly 120 includes valves that control the delivery of fluids to the endoscope 110 and a vacuum line that removes fluids and/or debris from the patient.

In some embodiments of the endoscopic preparation and examination system 100, the fluid/suction assembly 120 is removably disposed within a housing of the operator console 130. In other embodiments of the endoscopic preparation and examination system 100, one or more components of the fluid/suction assembly 120 are located externally to the operator console 130. In some embodiments, one or more components of the fluid/suction assembly 120 are made of low cost materials and are intended to be disposed of after a single use.

The operator console 130 is a special-purpose electronic and electro-mechanical apparatus that facilitates, processes and manages all functions of the endoscopic preparation and examination system 100. The operator console 130 includes an image processing CPU, an electrical connection to the endoscope 110, a connection to the user interface 134, and a connection to the fluid/suction assembly 120. The operator console 130 manages the operation of the pumps, including the vacuum pump 122 and the fluid pump 128 of the fluid/suction assembly 120 as well as managing the operation of the valves that control the fluid delivery to the endoscope 110 and the vacuum line that removes the fluid and debris from the patient. The operator console 130 is loaded with software for managing the operation of the endoscope 110 and its associated imaging electronics (not shown) to create and/or transfer images received from an image sensor at the distal end of the endoscope 110, to the display unit 136 for viewing by a user.

In the embodiment of the endoscopic preparation and examination system 100 shown in FIG. 1, the handheld controller 114 is a device that is electrically and fluidly connected to the distal shaft 112 and the proximal shaft 116 of the endoscope 112. The proximal shaft 116 carries the electrical and fluid connections to the fluid/suction assembly 120. The handheld controller 114 accepts user input via standard activation devices, such as, for example, push buttons, switches, rotary knobs, joysticks, keyboard, touch screen, or other activation devices, either singularly or in combination, to control the operation of the endoscope probe and to control the articulation of the distal tip via control wires (not shown).

Figure 2:
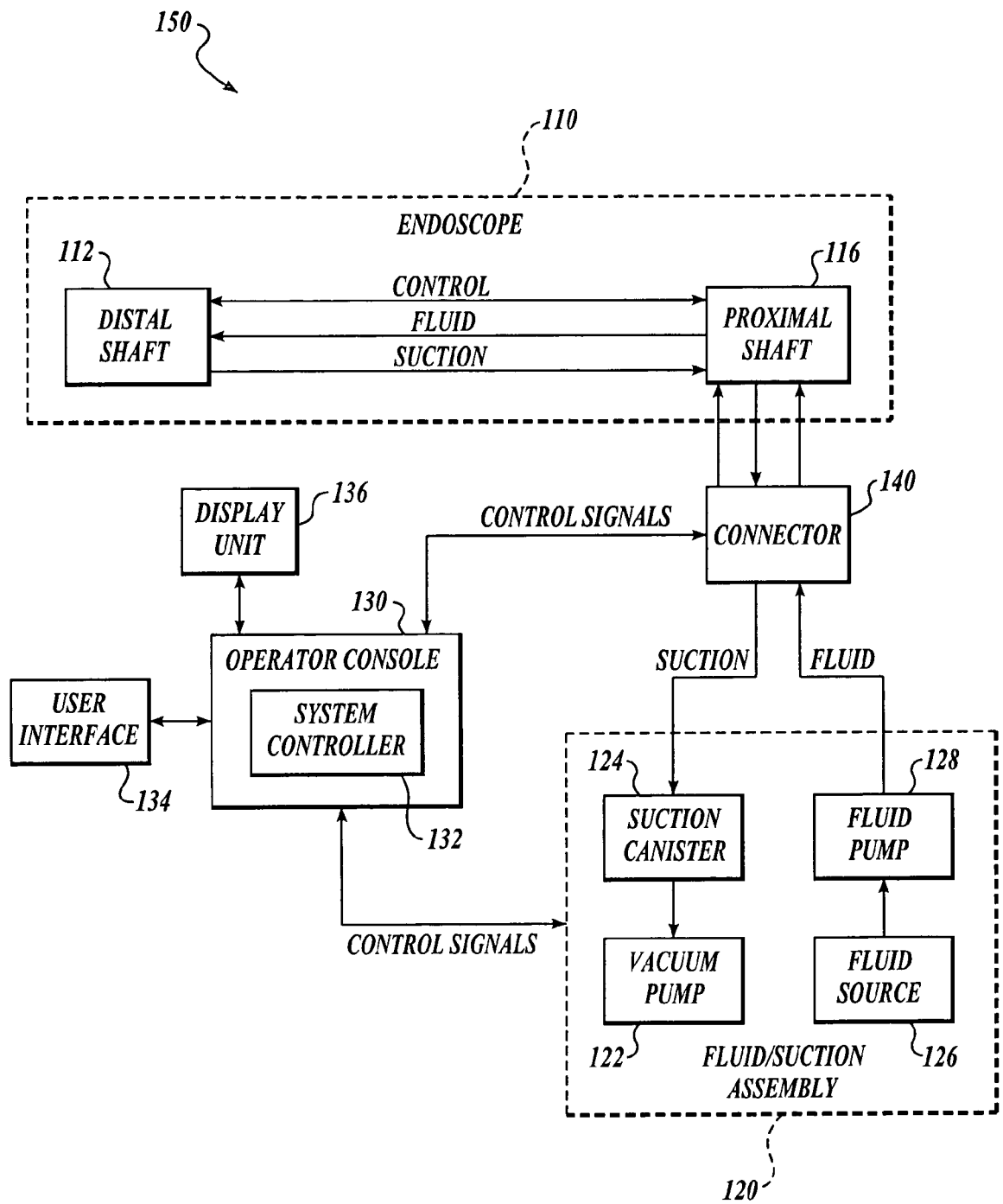
FIG. 2 is a block diagram of an endoscopic preparation and examination system comprising an endoscope, a fluid/suction assembly and an operator console in accordance with another embodiment of the invention.

FIG. 2 illustrates the major components of an alternative embodiment of an endoscopic preparation and examination system 150. The major features of the system 150 are substantially similar to the system 100 described above, with the addition of a connector 140 that functionally and electrically connects the proximal shaft 116 of the endoscope 110 to the fluid/suction assembly 120 and to the operator console 130 in order to carry fluid, suction, and control signals to the endoscope 110. In some embodiments of the system 150, the connector 140 is made of low cost materials and is intended to be disposed of after a single use.

The endoscope 110 is an instrument that allows for the preparation and optional examination of the interior of a canal or hollow organ of a patient. In one embodiment, the endoscope 110 is designed to be a preparation-specific endoscope with a plurality of suction and aspiration lumens and associated ports configured to allow for an increased capacity and/or rate of obstruction removal from a patient. In one embodiment, the endoscope 110 includes an imaging apparatus such as an objective lens and fiber optic imaging light guide communicating with a camera at the proximal end of the scope, or an imaging camera chip at the distal tip, that produces an image that is displayed to the operator. In one embodiment, the endoscope 110 is sufficiently inexpensive to manufacture, such that it is considered a single-use and disposable item. For example, the distal shaft 112 of the endoscope 110 may be formed of a suitably lightweight, flexible material, such as a polyurethane or other suitable biocompatible plastic material. The endoscope 110 comprises an elongated shaft that contains one or more lumens located therein and wiring located therein for the purpose of performing endoscopic procedures and facilitating the insertion and extraction of fluids, gases, mechanical devices and/or medical devices into and out of the body, as described in more detail below.

Figure 3A:
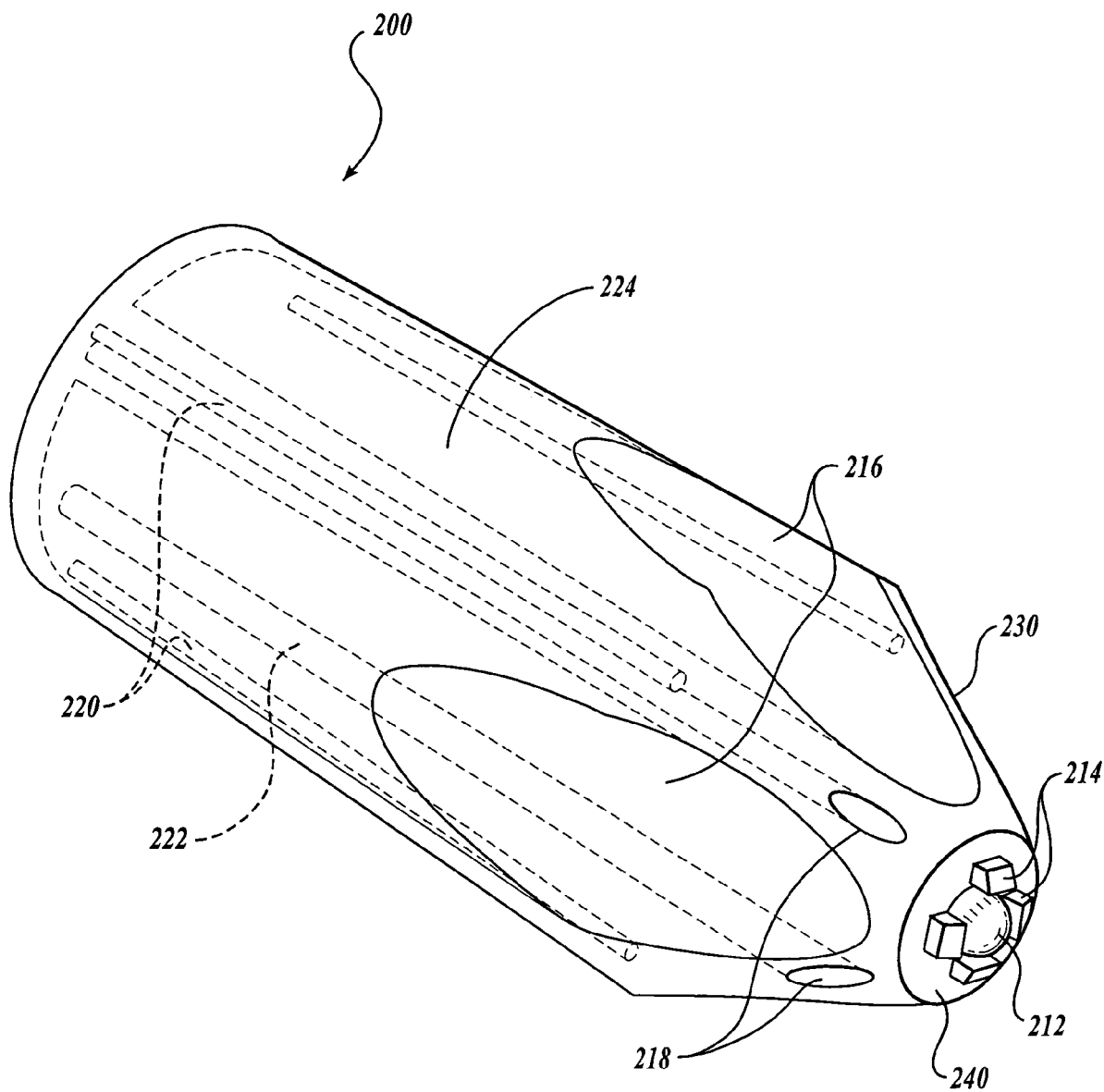
FIG. 3A is a perspective view showing a representative distal tip of an endoscope comprising a plurality of aspiration ports and a plurality of irrigation ports, in accordance with an embodiment of the invention.

FIG. 3A illustrates the main features of a distal tip 200 of the distal shaft 112 in accordance with an embodiment of the endoscope 110. The distal tip 200 includes a plurality of articulation wires 220 internally and circumferentially disposed around the distal tip 200 that are selectively tensioned and released to steer the distal tip 200. The distal tip 200 includes an image sensor apparatus 212, an illumination source, such as one or more light-emitting diodes (LEDs) 214, one or more distal aspiration/suction ports 216, and a plurality of distal fluid irrigation ports 218.

In one embodiment of the distal tip 200, a plurality of aspiration/suction ports 216, such as, for example, two, three, four or more aspiration/suction ports 216 open into one or more aspiration lumens 224 that run the length of the endoscope 110 and are connected to the vacuum line of the fluid/suction assembly 120. In the embodiment shown, the distal tip 200 of the endoscope 110 is generally cylindrical in shape, but a tapered portion 230 tapers to a flat surface 240 that is oriented perpendicular to the longitudinal axis of the endoscope 110. The aspiration/suction ports 216 are symmetrically located around and proximal to the flat surface 240. In the embodiment shown, each aspiration/suction port 216 is generally oval in shape with a length that is longer than the tapered portion 230 of the distal tip 200 such that debris can enter the aspiration/suction port 216 from a direction directly in front of the endoscope 110 as well as from the side of the distal tip 200. In the embodiment shown, the distal fluid irrigation ports 218 are also located around the flat surface 240 at positions between the aspiration/suction ports 216.

With continued reference to FIG. 3A, the image sensor apparatus 212 is mounted on the flat surface 240 at the distal tip 200 of the endoscope 110. The image sensor apparatus 212 includes electronics and an objective lens assembly that functions as the viewing port of the endoscope 110. The image sensor may be any suitable solid state imaging device, such as, for example, a complementary metal-oxide semiconductor (CMOS) chip or charge coupled device (CCD). In one embodiment of the distal tip 200, the image sensor apparatus 212 is surrounded by a plurality of LEDs 214, such as two, three, four or more LEDs. In one embodiment of the distal tip 200, an optically clear material, such as a glass or plastic nose cone, is used to encase the image sensor apparatus 212 and LEDs 214 (not shown). To prevent the distal tip 200 from becoming too hot, the LEDs may be connected to a heat sink (not shown) in thermal contact with the distal fluid ports 218 so that fluid delivered to the patient cools the LEDs. In other embodiments, separate lumens for providing a cooling liquid to the LEDs may be included in the endoscope 110. In some embodiments of the distal tip 200, additional external elements may be included, such as, for example, air ports.

In one embodiment of the distal tip 200, the plurality of irrigation fluid ports 218, such as, for example, two, three, four or more irrigation fluid ports 218 are spaced symmetrically around the distal tip 200, and may be positioned proximal to the LEDs 214. The irrigation fluid ports 218 open into one or more irrigation lumens 222 that run the length of the endoscope 110 and connect to the fluid delivery line of the fluid/suction assembly 120. The irrigation fluid ports 218 enable a large volume of irrigation fluid to be delivered to the region adjacent to the distal tip 200 of the endoscope 110. In one embodiment of the distal tip 200, at least one of the plurality of irrigation ports 218 exit the distal tip 200 in the tapered portion 230, thereby resulting in an oval-shaped orifice.

Figure 3B:
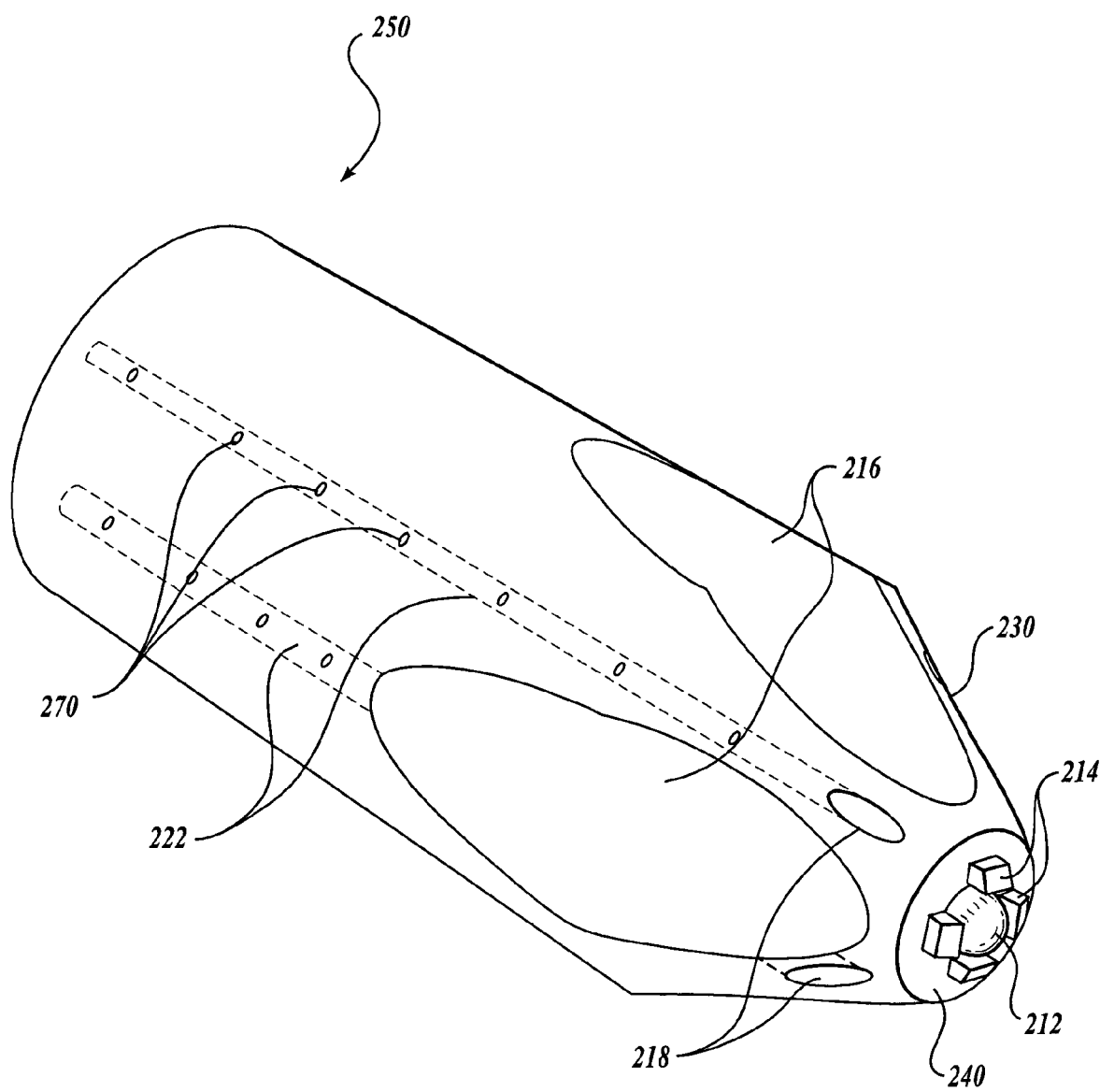
FIG. 3B is a perspective view showing a representative distal tip of an endoscope comprising a plurality of aspiration ports and a plurality of lateral irrigation ports, in accordance with an embodiment of the invention.

FIG. 3B illustrates another embodiment of a distal tip 250 containing at least one irrigation fluid lumen 222. The lumen 222 opens at one or more distal irrigation fluid ports 218 positioned at or near the distal-most end of the distal tip 250. The distal tip 250 further includes a plurality of lateral irrigation ports 270 spaced along the outer surface of the distal tip 250. Each lateral irrigation port 270 may include a spray nozzle (not shown) to allow irrigation fluid to be sprayed out laterally from the distal tip 250. The spray nozzle(s) may be adjustable to increase the velocity or pressure of the irrigation fluid flow and/or the direction of the fluid exiting the endoscope. The lateral irrigation ports 270 may be all open at the same time, or the ports 270 and/or nozzles may be regulated to deliver a selected irrigation pattern, such as from the distal to proximal end of the endoscope. For example, the fluid ports 270 and/or spray nozzles may further include a valve that is controllable from the operator console 130 or handheld controller 114 in order to regulate the irrigation in a selected pattern. Additionally, the ports 270, nozzles or fluid/suction assembly 120 may be regulated to deliver the irrigation fluid with a selected pulsation or frequency.

In another embodiment of the distal tip 250, a plurality of aspiration/suction ports, such as, for example, two, three, four or more aspiration/suction ports are spaced along the outer surface of the distal tip 250 (not shown). In a further embodiment of the distal tip 250, a plurality of lateral aspiration/suction ports and a plurality of lateral irrigation ports may be spaced along the outer surface of the distal tip 250 in various configurations in order to maximize the irrigation and aspiration of a body cavity of a patient.

In an alternative embodiment, the aspiration ports 216 are connected via a valve (not shown) to either the vacuum line or fluid line of the fluid/vacuum assembly 120. In such an embodiment, the aspiration ports 216 may act as either the fluid delivery mechanism or the aspiration mechanism, with the valve controlled by either an activation device on the handheld controller 114, or, alternatively, by a control signal from the operator console 130.

In operation, the aspiration ports 216, distal irrigation ports 218, and optional lateral irrigation ports 270 function together to deliver irrigation and aspiration modalities to a region of the body, such as the colon, as described in more detail below.

Figure 4:
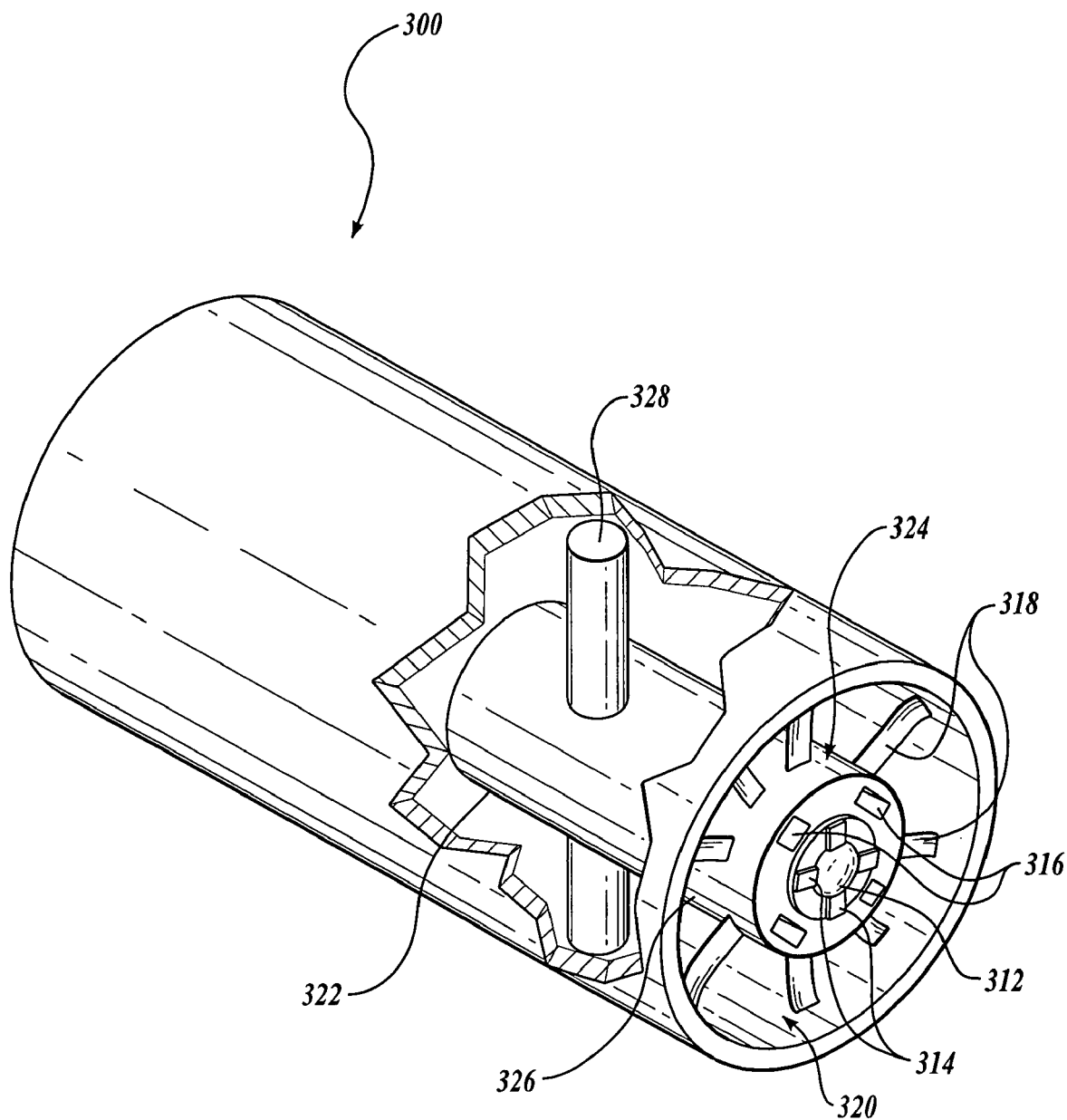
FIG. 4 illustrates the main features of an endoscope distal tip comprising an aspiration lumen containing an excising device in the form of a cutting blade structure in accordance with another embodiment of the invention.

FIG. 4 illustrates the main features of the distal tip 300 of a patient preparative and imaging endoscope in accordance with another embodiment of the invention. Internally, the distal tip 300 includes a plurality of articulation wires (not shown) that are secured at or adjacent the distal end to steer the endoscope in a desired direction. The external features of the distal tip 300 include an image sensor apparatus 312, an illumination source, such as one or more LEDs 314, and a plurality of distal irrigation ports 316. Additionally, the distal tip 300 contains an excising device 324 disposed therein. The excising device 324 may be fixedly disposed, or removably disposed in the distal tip 300. The excising device 324 may be movable to extend beyond the distal tip 300 of the endoscope and to retract into the distal tip 300. In one embodiment, the excising device 324 is disposed within at least one aspiration/suction port. The excising device 324 may be any device capable of mechanically cutting, ablating, liquefying and/or disrupting and removing an obstruction such as fecal matter, tissue, mucus, plaque, tumors or other material that can obstruct the physician's view or interfere with the endoscopic procedure. For example, the excising device 324 may include a cutting blade, vibrational cutter, abrasive member, wire cutter, jaws, claws, pinchers, snare, etc.

In the illustrative embodiment shown in FIG. 4, the excising device 324 comprises a plurality of macerator blades 318 that are attached to a macerator shaft 326 that is electrically and mechanically connected to a macerator mechanism 322. The macerator blades 318 are preferably centered on a supporting structure 328 attached to an interior portion of the walls of a suction lumen 320. In one embodiment, the macerator blades 318 are arranged in a screw-like formation to facilitate break up and removal of obstructing material. The suction lumen 320 is connected to the vacuum line of the fluid/suction assembly 120. The macerator mechanism 322 is the actuator by which the macerator blades 318 and/or the macerator shaft 324 are driven, i.e., a miniature electric, pneumatic, hydraulic motor capable of driving the macerator shaft 324 and/or blades 318. The macerator blades 318 rotate to break up large pieces of an obstruction, such as fecal material, or other debris, and thereby liquefy the obstruction by mechanical agitation, preferably in the presence of wetting fluid that is delivered from the fluid lumen (hidden from view) connected to the fluid/suction assembly 120 via the distal fluid aspiration ports 316. Other elements, such as air ports, are not shown, but may also be included as a part of distal end 300.

Figure 5A:
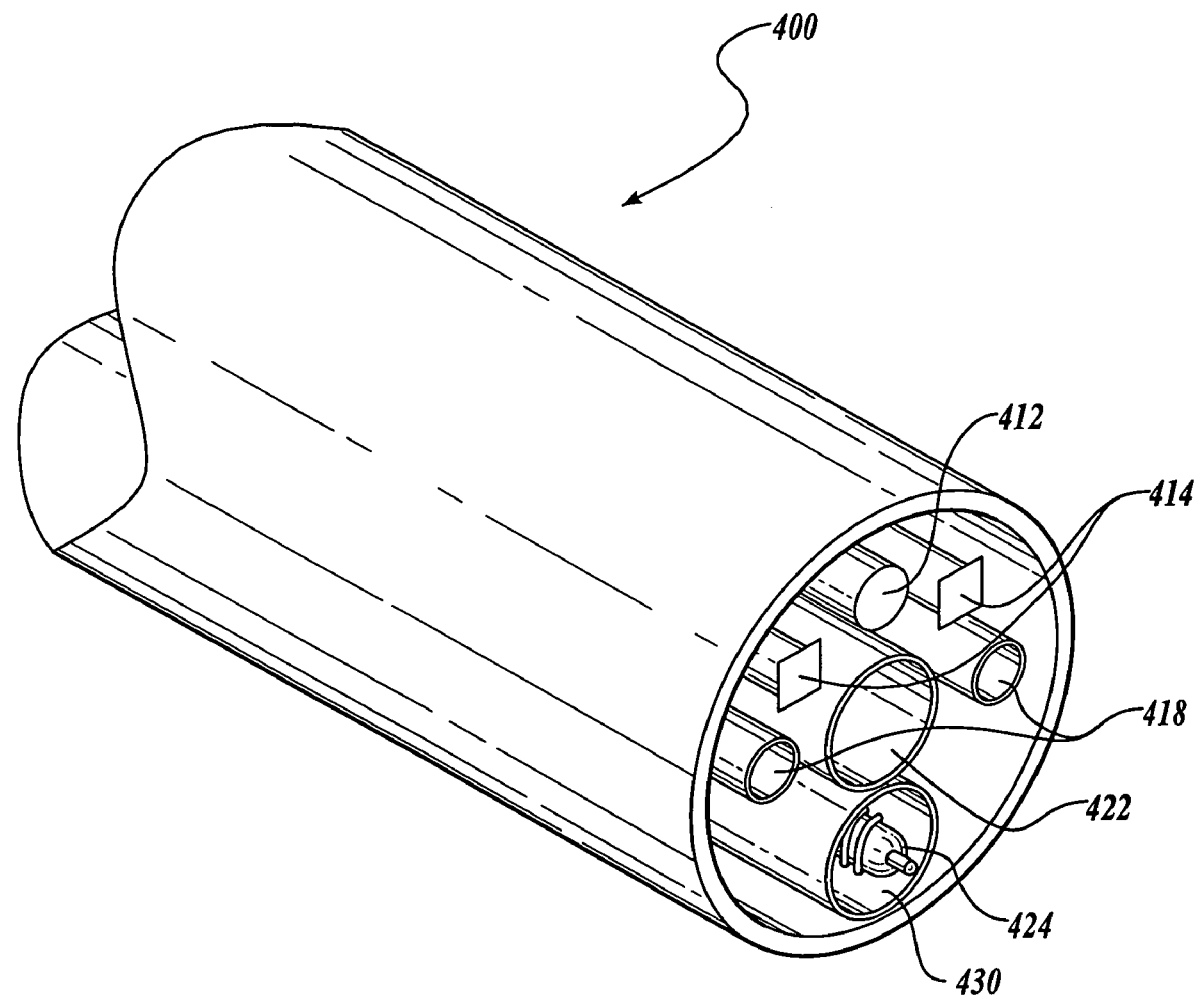
FIG. 5A illustrates the main features of an endoscope distal tip comprising a working channel port and an aspiration port including an excising device in accordance with another embodiment of the invention.

FIG. 5A illustrates the main features of another embodiment of a distal tip 400 of a patient preparation and examination endoscope 110. The external features of the distal tip 400 include an image sensor 412, an illumination source, such as one or more LEDs 414, and one or more irrigation ports 418. Further included in the distal tip 400 is an entrance to a working channel lumen 422 and at least one distal aspiration port 420. The working channel lumen 422 runs the length of the endoscope 110 and is accessible through a biopsy port (not shown) in the handheld controller 114, or via the proximal shaft 116, for the purpose of passing tools such as biopsy forceps, snares, fulgration probes, and other material to the distal tip 410. In the embodiment of the distal tip 400 shown in FIG. 5A, an excising device 424 in the form of a macerator is disposed within the aspiration lumen 430. While the excising device 424 shown in FIG. 5A extends out of the distal end of the endoscope, it will be appreciated that the excising device 424 may also be configured to exit laterally through a lateral opening in the shaft, such as, for example, a lateral aspiration/suction port 270 (see FIG. 3B).

Figure 5B:
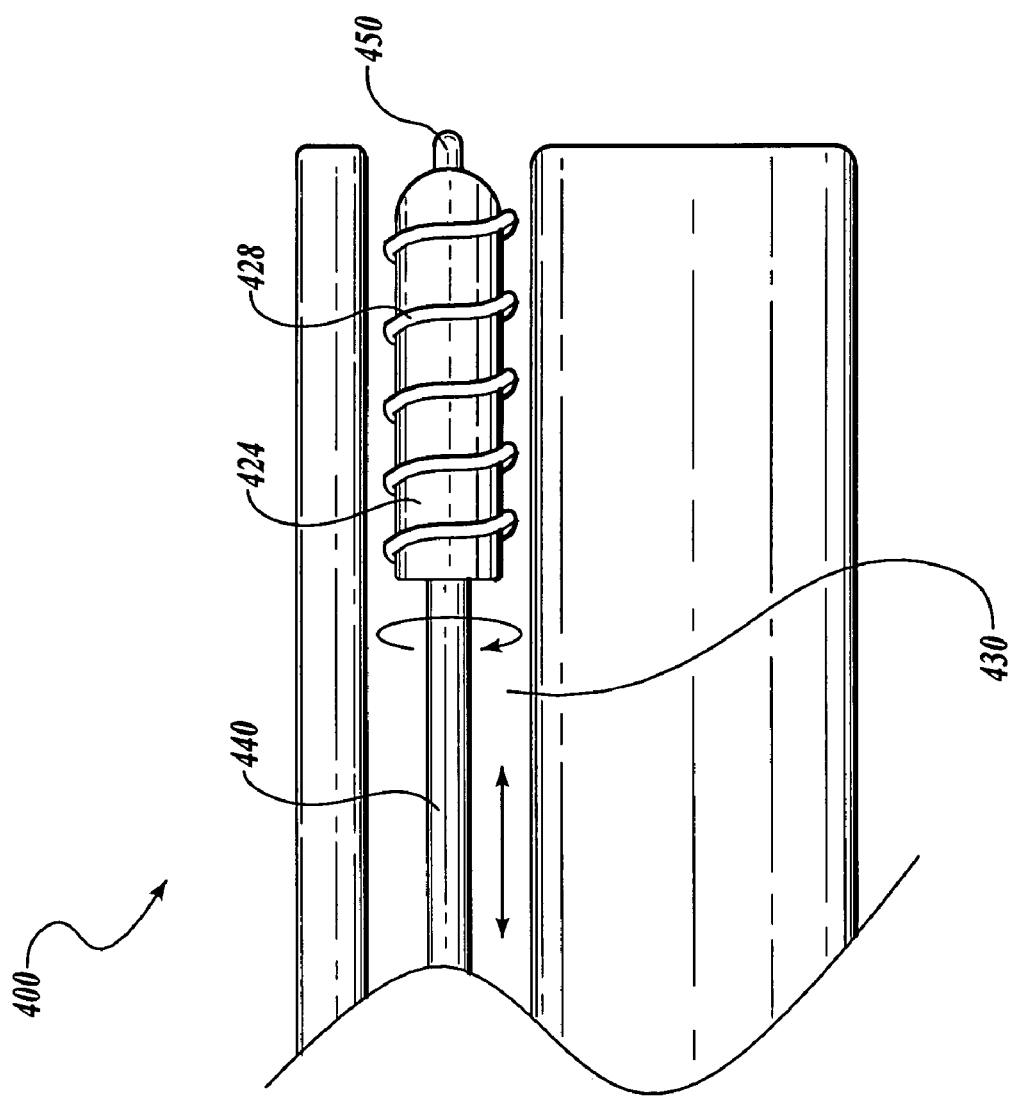
FIG. 5B shows a cross-sectional view along the longitudinal axis of the aspiration lumen of the distal tip shown in FIG. 5A, illustrating more detail of the excising device, in accordance with an embodiment of the invention.

As better shown in FIG. 5B, the excising device 424 comprises a plurality of macerator blades 428 that are attached at the distal end of a macerator shaft 440 that is removably or movably disposed inside the aspiration lumen 430. The excising device 424 may be extended beyond the distal tip 410 of the endoscope 110, or may be retracted into the distal tip 410, via controls on a user input device located on the handheld controller 114 or on the operator console 130. The macerator shaft 440 may further include an energy-emitting tip 450, that is capable of emitting energy such as vibration, fluid, electromagnetic energy, or ultrasonic energy to facilitate the mechanical breakup of an obstruction.

Figure 6A:
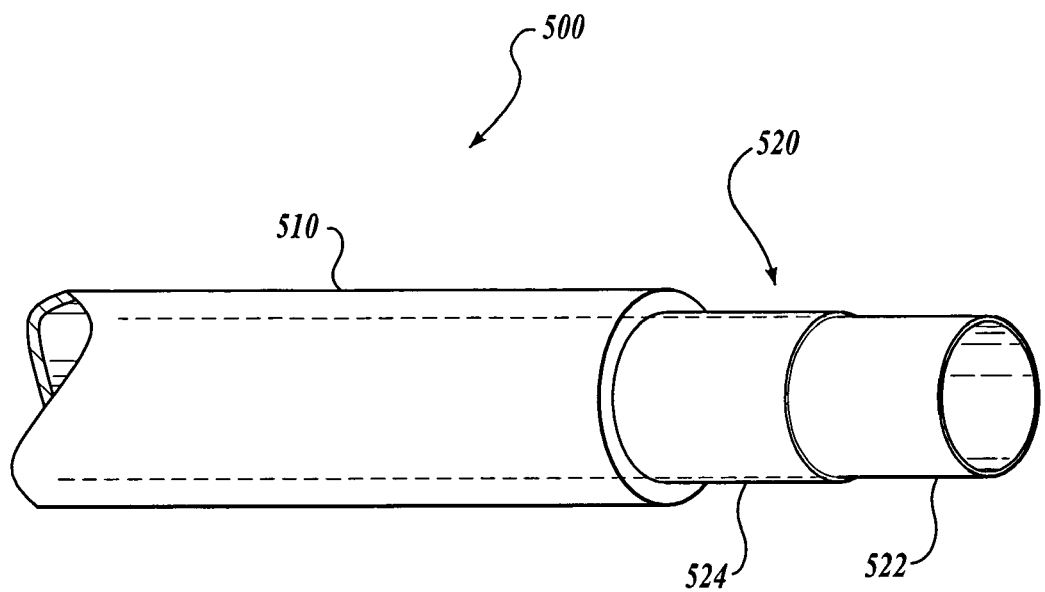
FIG. 6A illustrates one embodiment of a trapping device disposed within a distal tip of an endoscope, in accordance with an embodiment of the invention.

FIG. 6A illustrates yet another embodiment of the present invention that provides a patient preparation and examination endoscope 110 with a distal tip 500 including a trapping device 520. The trapping device 520 comprises an outer flexible portion 522 adapted to gently slide along the walls of a body cavity, such as a colon, and trap liquefied material. The outer flexible portion 522 is attached to an insertion tube 524 that is capable of extending and retracting the outer flexible portion 522 into and out of the distal tip 500. The outer flexible portion 522 may be in the form of any shape suitable for trapping and/or moving liquefied material, such as, for example, a tubular shape, a half-round shape, a scoop shape, etc. The trapping device 520 acts to move, draw in, secure and optionally aspirate material such as irrigants, or liquefied material including fecal matter, tissue, mucus, plaque, tumors or other material that can obstruct the physician's view or interfere with the endoscopic procedure. In one embodiment, the outer flexible portion 522 is made of an optically clear material in order to improve visualization of the region with an imaging apparatus during deployment of the trapping device 520. The trapping device 520 may be disposed within the outer wall of the distal tip 500, or, alternatively, the trapping device 520 may be disposed within a lumen positioned within the distal tip 500, such as an aspiration lumen or working channel lumen. In one embodiment, the trapping device 520 comprises an open-ended insertion tube 524 which extends to the proximal region of the endoscope 110 and is attached to the vacuum line in the fluid/suction assembly 120 and selectively controlled by the control unit 130.

Figure 6B:
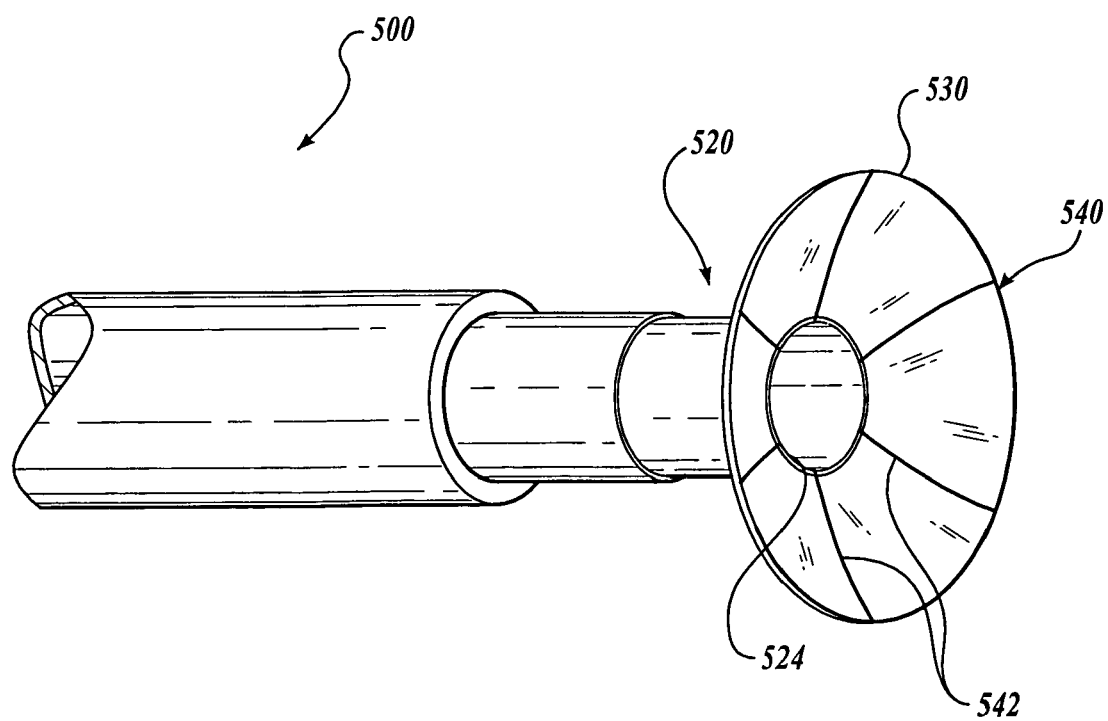
FIG. 6B illustrates an embodiment of the trapping device comprising an expandable and retractable distal portion.

FIG. 6B illustrates an embodiment of the trapping device 520 that further comprises an expandable outer flexible portion 530 that may be expanded and retracted circumferentially about the distal region of the endoscope 110. The expandable portion 530 may be expanded and contracted with any suitable mechanism, such as, for example, an umbrella-type frame 540 as shown in FIG. 6B. The umbrella frame 540 comprises an expandable outer rim 530 which is supported by a plurality of flexible struts 542. The struts 542 are slidably engaged in the insertion tube 524. The insertion tube 524 is in turn attached to a user input device, such as the handheld controller 114 via one or more control wires (not shown). The rim 530 and struts 542 can be made of a spring-like metal material or plastic (e.g., stainless steel, Nitinol, etc.) so that the rim 530 expands radially outward upon release from the insertion tube 524. Other methods of expanding and contracting the expandable region 530 may also be utilized, such as, for example, using an inflatable member.

In another aspect, the present invention provides a method of preparing a patient for an endoscopy procedure, such as a colonoscopy. For example, the method may be used to evacuate the colon or other area of poorly prepared patients or non-prepared patients preceding or during an endoscopy procedure.

With reference to FIGS. 1-6B, an exemplary process of irrigation and aspiration for the purpose of evacuation preceding a colonoscopy procedure by using the endoscope system 100, 150 is as follows:

A user, which may be a physician, nurse, or other assistant, attaches the patient preparation and examination endoscope 110 to the operator console 130. The user verifies that all required fluid or vacuum sources, such as those provided by fluid/suction assembly 120 or the like, are available, and activates the operator console 130.

The user selects an irrigation and aspiration modality via the user interface 134; the handheld controller 114, or, alternatively, the user programs a new wash routine by recording a series of operator commands on the user interface 134. The irrigation and aspiration modality may include a selection of one or more irrigation fluids, including, for example, heated fluid, fluid containing microparticles to break up obstructing materials, fluid containing emulsifying detergents, and the like.

In one example, a jet wash is delivered for a period of time, such as, for example, three seconds via the one or more irrigation ports 218 (FIG. 3A), followed by aspiration for a period of time, such as, for example, five seconds via the one or more aspiration ports 216 (FIG. 3A). A large bolus wash is then initiated for a period of time, such as, for example, three seconds, followed by aspiration for a period of time, such as, for example, five seconds. This process may be repeated until the obstruction is removed.

More specifically, the physician introduces distal shaft 112 into the patient's colon and advances it by using, for example, rotary knobs (not shown) of the handheld controller 114 or servo motor control, until such time that the target site may be visualized upon the display unit 136. As obstructions that interfere with the colonoscopy are detected, irrigation and/or mechanical maceration is initiated upon operator command, by means of the handheld controller 114, or the user input device 134 and excising device 324, 424. As a result, the system controller 132 activates the vacuum pump 122, the fluid pump 128 and/or macerator blades 318. Consequently, irrigant is channeled to the lumen(s) of the endoscope 110 and out of, for example, the irrigation ports 218 or 316 or 418, according to the modality selected by the user via user interface 134, i.e., jet wash or a large bolus wash. After irrigation, the resulting maceration is aspirated automatically, if a pre-defined modality is being used, or by operator command by means of the user interface 134, or the handheld controller 114, if a manual procedure is being executed. The trapping device 520 (FIGS. 6A, 6B) may also be deployed to aid in the entrapment and aspiration of the obstructing material. The user interface 134 causes the vacuum pump 122 to apply suction through the distal aspiration ports 216, 320 or 420 of the endoscope 110. In accordance with one embodiment, the endoscope 110 is designed as a preparation-specific device and after the colon preparation procedure is completed, the distal shaft 112 of the endoscope 110 is withdrawn from the patient, and the endoscope 110 is disconnected from control unit 130 via, for example, a quick-release mechanism. A second imaging endoscope is then attached to the control unit 130 for the examination of the patient. In accordance with another embodiment, the endoscope 110 is designed as a preparation and examination device, and after the preparation of the patient is completed, the endoscope 110 is then used to examine the patient for the presence of polyps, lesions, and the like. If the endoscope 110 is designed as a low cost single-use device, the endoscope 110 is properly disposed of as medical waste after removal from the patient. If the endoscope 110 is designed as a reusable medical device, after removal from the patient, it is cleaned and disinfected for the next use.

Figure 7:
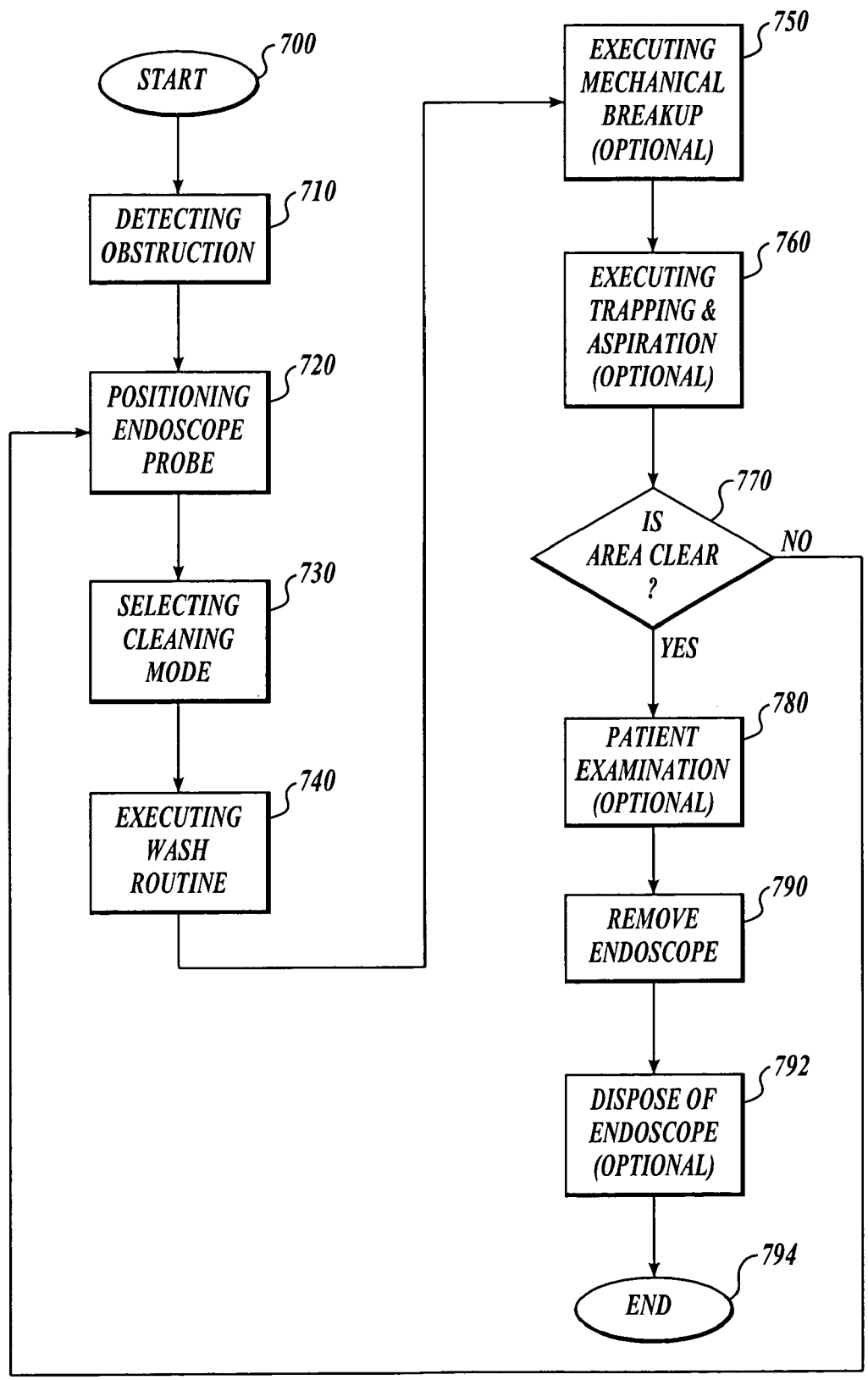
FIG. 7 is a flow diagram of a method of performing an irrigation and aspiration process with an endoscopic preparation and examination system in accordance with an embodiment of the present invention.

A representative processing routine for performing irrigation and aspiration in accordance with this aspect of the invention is shown in FIG. 7. The irrigation and aspiration starts at 700. At 710 an obstruction is detected on the display monitor. At 720 the operator steers the distal end 200, 250, 300, 400 or 500 of the distal shaft 112 to a location proximal to the obstruction, by using live endoscopic images received from the image sensor 212, 312 or 412 via the handheld controller 114, or the user input device 134. At 730 the user selects a pre-programmed wash routine, such as, for example, a sequence comprising a bolus wash and a jet wash, followed by aspiration, via a menu displayed on the display unit 136. Alternatively, a manual mode is selected. At 740 the selected wash routine is initiated upon operator command by means of handheld controller 114 or user input device 134. The wash routine may be pre-defined, or may be manually selected by the user, based on satisfactory or unsatisfactory results. System control software activates the appropriate pumps, such as the vacuum pump 122 and the fluid pump 128, and mechanical control mechanisms and valves, by action of the system controller 132. As a result, the wash routine selected at 730 is delivered. Aspiration is commenced, following irrigation, either automatically or under operator command by means of the handheld controller 114 or user input device 134. During aspiration, the system controller 132 activates the vacuum pump 122, whereby suction is applied through at least one lumen of the endoscope 110. The evacuated material is collected within the suction canister 124 by the action of the vacuum pump 122.

At 750 an optional mechanical breakup routine may be executed, for example, by activating the excising device 324 or 424 for the required duration of time.

At 760 an optional trapping and aspirating routine may be executed, for example, by deploying the trapping device 520 to trap the obstructing material and aspirating the trapped material.

At 770 the operator determines whether the colon is sufficiently clear for examination by viewing the live endoscopic images displayed on the display unit 136. If YES, the method 700 proceeds to block 780. If NO, the method 700 returns to block 720.

At 780 the operator optionally proceeds with an endoscopic examination of the patient which may include capturing images of the colon wall, capture of tissue samples, and/or therapeutic intervention.

At 790 the distal shaft 112 of the endoscope 110 is withdrawn from the patient by the operator. At 792, if the endoscope 110 is designed for a single use, it is disposed of by means of standard medical waste disposal procedures. The method ends at 794.

While the preferred embodiment of the invention has been illustrated and described, it will be appreciated that various changes can be made therein without departing from the scope of the invention.

The embodiments of the invention in which an exclusive property or privilege is claimed are defined as follows:

1. An endoscope system for clearing an obstruction in a patient, comprising:
    an elongated flexible shaft with a proximal end, a distal tip terminating distally at a forward face and having a tapered portion with a narrowest point at the forward face and a widest point proximal to the narrowest point, at least one aspiration lumen, and at least one irrigation lumen;
    wherein the shaft includes a plurality of irrigation ports functionally connected to the at least one irrigation lumen; and
    a plurality of aspiration ports functionally connected to the at least one aspiration lumen, wherein the plurality of aspiration ports are positioned around the circumference of the shaft and extend into the distal tip such that the aspiration ports are at least partly open to the side of the shaft and at least partly open to the distal tip, wherein the aspiration ports each have an opening with an edge defining the entire distal circumference of the aspiration port, the edge having a first end situated proximal to the widest point of the tapered portion and a second end situated between the widest point of the tapered portion and the narrowest point of the tapered portion; and
    wherein the at least one irrigation lumen is adapted to be connected to a source of irrigation and the at least one aspiration lumen is adapted to be connected to a source of aspiration at the proximal end of the shaft and wherein the sources are selectively controlled by a user input device to deliver an irrigant through the at least one irrigation lumen on the endoscope and to aspirate through the at least one aspiration lumen.

2. The endoscope system of claim 1, wherein at least one of the plurality of irrigation ports is located on the lateral surface of the longitudinal axis of the shaft.

3. The endoscope system of claim 1, wherein at least one of the plurality of irrigation ports is located on the distal tip of the shaft.

4. The endoscope system of claim 1, wherein the diameter of the at least one aspiration ports is at least twice the diameter of at least one of the irrigation ports.

5. The endoscope system of claim 1, wherein at least one of the plurality of irrigation ports is oval-shaped.

6. The endoscope system of claim 1, wherein at least one of the plurality of aspiration ports is oval-shaped.

7. The endoscope system of claim 1, further comprising an image sensor.

8. The endoscope system of claim 1, wherein the forward face is oriented perpendicular to the longitudinal axis of the endoscope.

9. The endoscope system of claim 8, wherein the image sensor is disposed on the forward face.

10. The endoscope system of claim 1, wherein the shaft is disposed of after a single use.

11. The endoscope system of claim 1, further comprising:
    an excising device disposed within the aspiration lumen, wherein the excising device includes a macerator shaft and a plurality of elongated macerator blades that extend radially from the macerator shaft, the elongated macerator blades being capable of mechanically cutting and/or disrupting an obstruction in a patient into a liquefied form for aspiration through the aspiration lumen while the macerator blades are positioned entirely within the aspiration lumen.

12. The endoscope system of claim 11, wherein the excising device is extendible beyond the distal tip of the shaft.

13. The endoscope system of claim 11, wherein the excising device further includes an energy emitting device.

14. The endoscope system of claim 11, wherein the shaft is disposed of after a single use.

15. The endoscope system of claim 11, wherein only one end of each of the plurality of elongated macerator blades is attached to the macerator shaft.

16. The endoscope system of claim 11, wherein a distance between a distal end of the macerator shaft and each of the plurality of elongated macerator blades is the same.

17. The endoscope system of claim 1, wherein a distance between the distal end of the distal tip and each of the plurality of aspiration ports is the same.

* * * * *

UNITED STATES PATENT AND TRADEMARK OFFICE
CERTIFICATE OF CORRECTION

| | | |
|---|---|---|
| PATENT NO. | : 8,353,860 B2 | Page 1 of 1 |
| APPLICATION NO. | : 11/241829 | |
| DATED | : January 15, 2013 | |
| INVENTOR(S) | : Boulais et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Thirteenth Day of January, 2015

Michelle K. Lee
*Deputy Director of the United States Patent and Trademark Office*